United States Patent
Monkman et al.

(10) Patent No.: US 11,725,013 B2
(45) Date of Patent: Aug. 15, 2023

(54) THERMALLY ACTIVATED DELAYED FLUORESCENCE MOLECULES, MATERIALS COMPRISING SAID MOLECULES, AND DEVICES COMPRISING SAID MATERIALS

(71) Applicant: THE UNIVERSITY OF DURHAM, Durham (GB)

(72) Inventors: Andrew P. Monkman, Durham (GB); Jonathan S. Ward, Durham (GB); Martin R. Bryce, Durham (GB); Daniel G. Congrave, Durham (GB); Lays Dos-Santos, Durham (GB)

(73) Assignee: The University of Durham, Durham (GB)

( * ) Notice: Subject to any disclaimer, the term of this patent is extended or adjusted under 35 U.S.C. 154(b) by 501 days.

(21) Appl. No.: 16/756,285

(22) PCT Filed: Oct. 17, 2018

(86) PCT No.: PCT/GB2018/052998
§ 371 (c)(1),
(2) Date: Apr. 15, 2020

(87) PCT Pub. No.: WO2019/077352
PCT Pub. Date: Apr. 25, 2019

(65) Prior Publication Data
US 2020/0331924 A1 Oct. 22, 2020

(30) Foreign Application Priority Data
Oct. 19, 2017 (GB) ...................................... 1717193

(51) Int. Cl.
*C07D 487/14* (2006.01)
*C09K 11/06* (2006.01)
(Continued)

(52) U.S. Cl.
CPC ............ *C07D 487/14* (2013.01); *C09K 11/06* (2013.01); *H10K 50/11* (2023.02); *H10K 85/6572* (2023.02); *H10K 85/6576* (2023.02)

(58) Field of Classification Search
CPC ...... C07D 487/14; C09K 11/06; H10K 50/11; H10K 85/6572; H10K 85/6576; H10K 2101/20
See application file for complete search history.

(56) References Cited

U.S. PATENT DOCUMENTS

| 2007/0191455 A1 | 8/2007 | Hiyoshi et al. |
| 2013/0056716 A1* | 3/2013 | Cheng ................. H01L 51/0085 546/10 |

(Continued)

FOREIGN PATENT DOCUMENTS

| CN | 106432251 A | 2/2017 |
| DE | 102016122122 A1 | 5/2017 |

(Continued)

OTHER PUBLICATIONS

Kwang Jong Kim et al "A new rigid diiondolocarbazole donor moiety for high quantum efficiency thermally activated delayed fluorescence emitter", Journal of Materials Chemistry C, vol. 6, No. 6, Jan. 1, 2018, pp. 1343-1348.

(Continued)

*Primary Examiner* — Su C Kim
(74) *Attorney, Agent, or Firm* — Harness, Dickey & Pierce PLC (57) ABSTRACT

A thermally activated delayed fluorescence (TADF) molecule comprising: a central electron donor moiety, wherein the central electron donor moiety is formed of a conjugated multi-ring system comprising three nitrogen atoms; and three electron acceptor moieties, each bonded to the central electron donor moiety via one of the three nitrogen atoms, wherein at least one of the three electron acceptor moieties (Continued)

is twisted relative to the central electron donor moiety defining a torsion angle in a range 40° to <90° whereby the TADF molecule has a photoluminescence quantum yield of >60% and a rate of reverse intersystem crossing from a lowest excited triplet state to a lowest excited singlet state of at least $1 \times 10$ s$^{-1}$.

26 Claims, 8 Drawing Sheets

(51) Int. Cl.
  *H10K 50/11* (2023.01)
  *H10K 85/60* (2023.01)

(56) References Cited

U.S. PATENT DOCUMENTS

| | | | |
|---|---|---|---|
| 2014/0084273 A1* | 3/2014 | Nakayama | H01L 51/0071 257/40 |
| 2016/0380203 A1* | 12/2016 | Jenekhe | H01L 51/0037 252/500 |
| 2017/0320855 A1* | 11/2017 | Wong | C07D 403/06 |

FOREIGN PATENT DOCUMENTS

| WO | WO-2014046221 A1 | 3/2014 |
|---|---|---|
| WO | 2016017684 A1 | 2/2016 |

OTHER PUBLICATIONS

Thanachart Techajaroonjit et al "Synthesis, characterization, and hole-transporting properties of pyrenyl N-substituted triazatruxenes", RSC Advances, vol. 6, No. 61, Jan. 1, 2016, pp. 56392-56398.

Kasparas Rakstys et al "Molecular engineering of face-on oriented dopant-free hole transporting material for perovskite solar cells with 19% PCT", Journal of Materials Chemistry A, vol. 5, No. 17, Jan. 1, 2017, pp. 7811-7815.

International Search Report and Written Opinion issued in PCT/GB2018/052998, dated Apr. 1, 2019; ISA/EP.

Gaozhan Xie et al., "Evaporation- and Solution-Process-Feasible Highly Efficient Thianthrene-9,9', 10,10'-Tetraoxide-Based ThermallyActivated Delayed Fluorescence Emitters with Reduced Efficiency Roll-Off," Advanced Materials, vol. 28, 2016, pp. 181-187.

Thanachart Techajaroonjit et al., "Synthesis, characterization, and hole-transporting properties of pyrenyl *N*-substituted triazatruxenes," RSC Advances, vol. 6, Jun. 7, 2016, pp. 56392-56398.

Eva M. Garcia-Frutos et al., Self-Assembly of C3-Symmetrical Hexaaryltriindoles Driven by.

Won Young Park et al., "Efficiency improvement opportunities for personal computer monitors: implications for market transformation programs," Energy Efficiency (2013), Jan. 23, 2013, pp. 545-569.

Fernando B. Dias et al., "Triplet Harvesting with 100% Efficiency by Way of Thermally Activated Delayed Fluorescence in Charge Transfer OLED Emitters," Advanced Materials, vol. 25, 2013, pp. 3707-3714.

Qisheng Zhang et al., "Design of Efficient Thermally Activated Delayed Fluorescence Materials for Pure Blue Organic Light Emitting Diodes," Journal of the American Chemical Society, vol. 134, Aug. 29, 2012, pp. 14706-14709.

Keigo Sato et al., "Organic Luminescent Molecule with Energetically Equivalent Singlet and Triplet Excited States for Organic Light-Emitting Diodes," American Physical Society, Jun. 10, 2013, pp. 247401-1-247401-5.

Ji Han Kim et al., "A novel pyrrolocarbazole donor for stable and highly efficient thermally activated delayed fluorescent emitters," Dyes and Pigments, vol. 136, Sep. 6, 2016, pp. 529-534.

Dongdong Zhang et al., "Highly Efficient Full-Color Thermally Activated Delayed Fluorescent Organic Light-Emitting Diodes: Extremely Low Efficiency Roll-Off Utilizing a Host with Small Singlet-Triplet Splitting," ACS Applied Materials & Interfaces, vol. 9, Jan. 17, 2017, pp. 4769-4777.

Inho Lee et al., "Molecular design of deep blue fluorescent emitters with 20% external quantum efficiency and narrow emission spectrum," Organic Electronics, vol. 29, Dec. 20, 2015, pp. 160-164.

Ting-An Lin et al., "Sky-Blue Organic Light Emitting Diode with 37% External Quantum Efficiency Using Thermally Activated Delayed Fluorescence from Spiroacridine-Triazine Hybrid," Advanced Materials, vol. 28, 2016, pp. 6976-6983.

Paloma L. dos Santos et al., "Using Guest-Host Interactions to Optimize the Efficiency of TADF OLEDs," The Journal of Physical Chemistry Letters, vol. 7, 2016, pp. 3341-3346.

Mark K. Etherington et al., "Revealing the spin-vribronic coupling mechanism of thermally activated delayed fluorescence," Nature Communications, Nov. 30, 2016, pp. 1-7.

Jamie Gibson et al., "The Importance of Vibronic Couplling for Efficient Reverse Intersystem Crossing in TADF molecules," ChemPhysChem, 2016, pp. 1-9.

Jonathan S. Ward et al., "The interplay of thermally activated delayed fluorescence (TADF) and room temperature organic phosphorescence in sterically-constrained donor-acceptor charge-transfer molecules," Royal Society of Chemistry, Jan. 11, 2016, pp. 3-6.

Hiroyuki Tanaka et al., "Twisted Intramolecular Charge Transfer State for Long-Wavelength Thermally Activated Delayed Fluorescence," Chemistry of Materials, Sep. 2, 2013, vol. 25, 3766-3771.

Xiang-Chun Li et al., "Triazatruxene-based materials for organic electronics and optoelectronics," Journal of Materials Chemistry C, vol. 4, Oct. 7, 2016, pp. 10574-10587.

Chinese Notice of Second Office Action, which corresponds to Chinese Patent Application No. 201880068138.1, dated Apr. 27, 2023 (8 Pages).

* cited by examiner

THERMALLY ACTIVATED DELAYED FLUORESCENCE MOLECULES, MATERIALS COMPRISING SAID MOLECULES, AND DEVICES COMPRISING SAID MATERIALS

CROSS-REFERENCE TO RELATED APPLICATIONS

This application is a 371 U.S. National Phase of International Application No. PCT/GB2018/052998, filed Oct. 17, 2018, which claims priority to British Patent Application No. 1717193.5, filed Oct. 19, 2017. The entire disclosures of the above applications are incorporated herein by reference.

FIELD OF INVENTION

The present invention is directed to thermally activated delayed fluorescence (TADF) molecules, materials comprising said molecules, and devices comprising said materials.

BACKGROUND OF INVENTION

Figure 1:
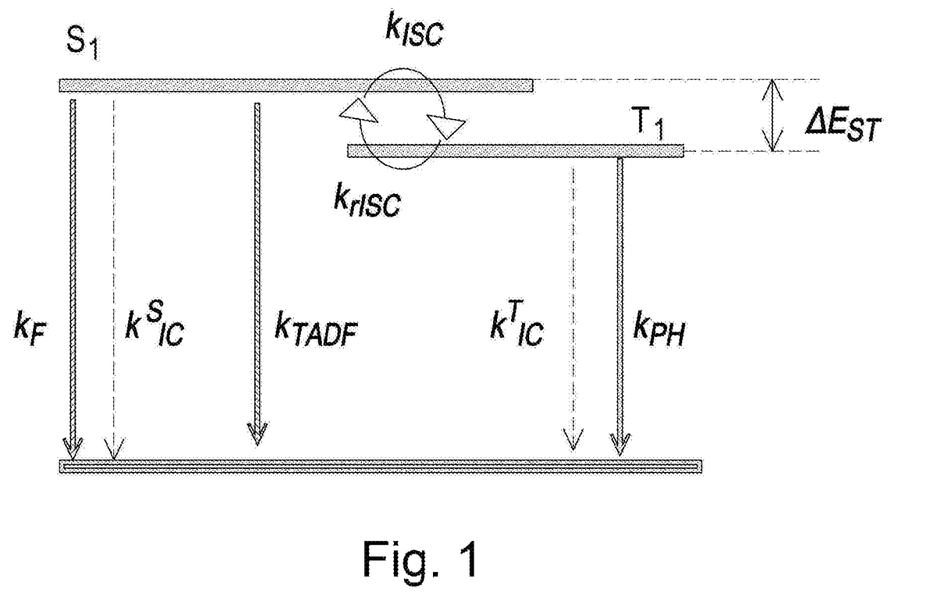
FIG. 1 shows a simplified representation of the electronic energy levels and rate constants involved in the TADF kinetic mechanism.

Organic light emitting diodes (OLEDs) have become a central part of materials chemistry research, with the ever growing requirement for more efficient, higher quality display devices. Driven by this, there is significant interest in organic OLED materials which emit light via a thermally activated delayed fluorescence (TADF) mechanism. By this mechanism, dark, triplet excited states are converted to emissive singlet states by efficient reverse intersystem crossing (rISC), using aromatic donoracceptor (D-A) molecules, which typically are conjugationally separated with the D and A units orthogonal. These systems typically emit from a singlet charge transfer state ($^1$CT), but require a local excited triplet state ($^3$LE) to be situated very close in energy to this $^1$CT. FIG. 1 shows a simplified representation of the electronic energy levels and rate constants involved in the TADF kinetic mechanism. rISC can in principle harvest up to 100% of triplet states into singlet states. This then can yield highly efficient devices in which the 75% excited states that have triplet character, and which typically would not emit in a pure organic material, are converted into emissive singlet states.

Within the past five years, many new TADF based emitters have been synthesised providing OLEDs having external quantum efficiencies exceeding 20%. Recently the present inventors have shown that the underlying spin flip mechanism in rISC is a second order vibrational coupling spin orbit coupling process where certain molecular vibrations drive coupling between the $^3$LE and $^3$CT states causing a thermal equilibrium between these two states. These coupled triplet states can then spin orbit couple to the $^1$CT state. The $^3$LE state acts as a mediator for both steps with vibrational energy driving the reverse intersystem crossing. Thus it is a thermal activated process. Certain vibrational modes are required for efficient rISC, and others contribute more to non-radiative decay. Different molecules will have a different assembly of allowed vibrations due to structure and symmetry, and therefore a different rISC rate can be observed. A useful review article describing the photophysics of thermally activated delayed fluorescence molecules is provided by F. B. Dias, T. J. Penfold and A. P. Monkman [Methods. Appl. Fluoresc. 5 (2017) 012001].

Previously synthesised 1-substituted phenothiazine D-A-D TADF candidates show molecular restriction with several conformers in solution on a $^1$H NMR (nuclear magnetic resonance) timescale. As well as the phenothiazine donor being tilted, it is clear there is some rotational restriction around the C—N bond in these systems, which switches off TADF due to the lack of vibronic coupling. The conformation of the phenothiazine with respect to the acceptor is also important in these molecules, and all of these factors must be taken into account when considering new molecular designs.

A typical configuration found in current TADF emitters comprises a central acceptor unit surrounded by peripheral donor units. An example of such a configuration is triphenoxazine-2,4,6-triphenyl-1,3,5-triazine (Tri-PXZ-TRZ) which was prepared by Tanaka and co-workers and has a central triazine acceptor unit and three phenoxazine donor units. This work shows the benefits of symmetry as the PXZ-TRZ and bis-PXZ-TRZ analogues showed lower device efficiency compared to the $C_3$ symmetric Tri-PXZ-TRZ.

While a typical configuration found in current TADF emitters comprises a central acceptor unit surrounded by peripheral donor units, there seems to be a small number of prior art disclosures of the opposite configuration in which a central donor unit is surrounded by peripheral acceptor units. For example, two published patent applications have been found which disclose the use of a central core truxene donor unit which is N-substituted with acceptor moieties: DE102016122122; and CN106432251. However, the TADF emitters disclosed in these documents do not seem to have particularly outstanding functional performance characteristics.

DE102016122122 appears to disclose a large number of potential molecules which are purported to exhibit thermally activated delayed fluorescence and have photoluminescence quantum yields of 30% or more including at least one example which comprises a central core triazatruxene donor moiety. However, all examples in DE102016122122 seem to have a photoluminescence quantum yield (PLQY) of around only 50% or less. It would be advantageous to provide TADF emitter molecules with a higher PLQY. It is also notable that all examples in DE102016122122 have emission decay times in the range 3 to 65 las. This is typical of the usual delayed fluorescence lifetimes of TADF emitters in the microsecond timeframe. It would be advantageous to provide TADF emitter molecules with shorter emission decay times indicative of a faster reverse intersystem crossing (rISC) and more efficient thermally activated delayed fluorescence.

CN106432251 discloses a triazatruxene type structure as illustrated in Formula 1 of the document. It is described that that the material exhibits thermally activated delayed fluorescence and that the material has a small A.$E_{ST}$ resulting in triplet to singlet reverse inter-system crossing thus enhancing efficiency. However, it is clear from the data provided in CN106432251 that although $\Delta E_{ST}$ is small (0.01 eV), the efficiency of the molecules is very low giving an external quantum efficiency (EQE) of only 3.36%. It would be advantageous to provide a TADF emitter which provides an increased external quantum efficiency.

Other prior art molecular systems are disclosed in EP2284920, WO2014/046221, WO2016/083655, WO2012/159213, CN101250404, and in Chemistry—A European Journal, vol. 14, no. 28, 2008, E. M. Garcia-Frutos et al. "Synthesis and preferred all-syn conformation of C3-symmetrical N-(hetero)arylmethyl triindoles", pp. 8555-8561. However, none of the molecular systems provide TADF emitters with sufficiently short emission decay times in combination with efficient thermally activated delayed fluorescence.

In light of the above, it is evident that there is an ongoing need to provide TADF emitters with high internal quantum efficiency. There is a further need to provide TADF emitters which provide a high photoluminescence quantum yield, particularly in a solid state host. There is a further need to provide TADF emitters which enable devices to be fabricated with increased external quantum efficiency. In this regard, efficient TADF molecules have to simultaneously satisfy the conditions of a small energy gap between the singlet and triplet excited states ($\Delta E_{ST}$), a vibrational structure which results in a fast rate of reverse intersystem crossing, and a structure which results in minimal non-radiative decay, thus maximising quantum efficiency and fluorescence yield.

It is a further desired to provide TADF emitters with increased stability and lifetime. Yet a further desire is to provide TADF emitters with increased brightness levels. It is further desirable to provide TADF emitters with a more efficient roll-off, i.e. the external quantum efficiency decreases less on increasing brightness levels. It is also desirable that target TADF emitters are soluble allowing efficient purification and synthesis with high yields. It is further desired to provide materials comprising TADF emitter—solid state host combinations which provide such improved performance characteristics and devices comprising such materials.

It is an aim of the present invention to address these issues.

SUMMARY OF INVENTION

A key challenge in the design of TADF molecules is to balance the rates of reverse intersystem crossing (rISC) and intersystem crossing (ISC) with the fluorescence quantum yield ($\Phi_F$). Ideally the desired molecule should have a $\Phi_F$ close to 1 (i.e. close to 100% photoluminescence quantum yield) to avoid decay by non-radiative pathways. This requires strong coupling of the $^1$CT to the ground state. However, to ensure a very small energy gap between $^1$CT and $^3$CT, a requirement for efficient rISC, donor-emitter orthogonality is required which effectively decouples the CT states from the ground state. Thus a compromise is required in TADF molecules between efficient rISC and non-radiative quenching to the ground state. TADF molecules are described herein which provide a suitable compromise between these features leading to improved functional performance.

According to one aspect of the invention as described herein there is provided a TADF molecule comprising:
 a central electron donor moiety, wherein the central electron donor moiety is formed of a conjugated multi-ring system comprising three nitrogen atoms; and
 three electron acceptor moieties, each bonded to the central electron donor moiety via one of the three nitrogen atoms,
 wherein at least one of the three electron acceptor moieties is twisted relative to the central electron donor moiety defining a torsion angle in a range 40° to <90° whereby the TADF molecule has a photoluminescence quantum yield of >60%, >70%, >80%, >90%, or >95% and a rate of reverse intersystem crossing from a lowest excited triplet state to a lowest excited singlet state of at least $1 \times 10^6$ s$^{-1}$, $5 \times 10^6$ s$^{-1}$, or $1 \times 10^7$ s$^{-1}$.

In relation to the above, it should be noted that the parameters of torsion angle, photoluminescence quantum yield, and rate of reverse intersystem crossing are readily measurable by a person skilled in the art based on the details given in the present specification, the cited references, and common general knowledge in the art. As such, for any given molecular system comprising a central electron donor moiety (formed of a conjugated multi-ring system comprising three nitrogen atoms) and three electron acceptor moieties (each bonded to the central electron donor moiety via one of the three nitrogen atoms), the molecular system can be readily tested to determine whether it falls within the scope of the aforementioned definition without undue burden. The present inventors are aware of a number of prior art molecules which have some similarities to the molecules of the present invention (e.g. those discussed in the background section). However, none of these have been found to meet the required combination of torsion angle, photoluminescence quantum yield, and rate of reverse intersystem crossing from a lowest excited triplet state to a lowest excited singlet state as defined above.

The present invention is based on an improved understanding of the functionality of TADF emitters and, in particular, the understanding to select moieties which twist relative to the central electron donor moiety to define a suitable torsion angle and thus provide a good compromise between $^1$CT ground state coupling for high photoluminescence quantum yield, while not opening up a significant $^1$CT-$^3$CT gap, thus resulting in fast reverse intersystem crossing and more efficient, thermally activated, delayed fluorescence. TADF molecules, as defined above, thus exhibit both a high photoluminescence quantum yield and a high rate of reverse intersystem crossing. The invention is not limited to a specific electron acceptor moiety structure, as different electron acceptor moieties could be incorporated into the molecular system in order to achieve the structure and function parameters as defined above.

At least two, and optionally all three, of the three electron acceptor moieties can be twisted relative to the central electron donor moiety defining suitable torsion angles. The donor and acceptor moieties can be selected such that the torsion angle is at least 40°, 50° or 60°, no more than 85°, 80°, or 70°, or within a range defined by any of the aforementioned lower and upper limits.

It has been found that the provision of such structures leads to a good compromise between $^1$CT ground state coupling for high photoluminescence quantum yield while not opening up a significant $^1$CT-$^3$CT gap thus resulting in fast reverse intersystem crossing and more efficient thermally activated delayed fluorescence. TADF molecules as described herein thus exhibit both a high photoluminescence quantum yield and a high rate of reverse intersystem crossing.

The TADF molecules advantageously have a plurality of singlet-triplet resonances within a 0.2 eV energy gap. Furthermore, the TADF molecules advantageously have at least one pair of singlet charge transfer and triplet charge transfer states within 0.05 eV. The provision of molecules which have singlet charge transfer, triplet charge transfer, and acceptor local states all within 0.2 eV of each other, preferably with at least one pair of states within 0.05 eV, gives highly efficient reverse intersystem crossing.

It has been found that because of the multiple resonance effects through all the available $S_1$-$S_0$ transitions from the three different donor-acceptor pairs, and further enhancement associated with the donor-acceptor torsion angles being somewhat less than 90° yielding significantly more coupling to the ground state, fast rate of reverse intersystem crossing leads to very short delayed fluorescence decay time. For example, the TADF molecules can have at least one delayed fluorescence decay time of less than 1 microsecond, less than 0.5 microseconds, and can even exhibit delayed fluorescence decay times of less than 0.2 microseconds.

An example of a central electron donor moiety which contributes to providing the aforementioned features is a triazatruxene moiety. The central electron donor moiety may consist of triazatruxene without any further functional groups bonded to carbon atoms of the conjugated multi-ring system. Alternatively, the central electron donor moiety comprises one or more functional groups bonded to one or more carbon atoms of the conjugated multi-ring system in addition to the three electron acceptor moieties bonded to the nitrogen atoms of the conjugated multi-ring system. The central donor moiety may be functionalized to tune its emission characteristics and/or the molecules solubility/processability.

The electron acceptor moieties can each be formed of a conjugated multi-ring system selected such that at least one, optionally two or all three, of the electron acceptor moieties is twisted relative to the central electron donor moiety defining the torsion angle in the range 40° to <90°. Furthermore, the electron acceptor moieties can each be formed of conjugated multi-ring systems selected such that the TADF molecule has a plurality of singlet-triplet resonances within 0.2 eV with at least one pair of singlet charge transfer and triplet charge transfer states within 0.05 eV. An example of such an electron acceptor moiety is dibenzothiophene-S,S-dioxide ($DBTO_2$).

It has also been found that the substitutional position (on the electron acceptor moieties) of the bond between the central electron donor moiety and the electron acceptor moieties can affect how the electron acceptor moieties are twisted relative to the central electron donor moiety to define the torsion angle in the range 40° to <90° and achieve the required photoluminescence quantum yield and rate of reverse intersystem crossing. In particular, it has been found that for certain configurations it is preferred that the electron acceptor moieties are para substituted rather than meta substituted. For example, in the aforementioned molecular system including a central triazatruxene moiety surrounded by dibenzothiophene-S,S-dioxide ($DBTO_2$) electron acceptor moieties, each (or at least one) $DBTO_2$ moiety is para substituted such that the bond to the nitrogen of the triazatruxene is in a para position relative to the sulphur atom of the $DBTO_2$ moiety. This para coupled version provides a torsion angle in the range 40° to <90° and achieves the required photoluminescence quantum yield and rate of reverse intersystem crossing. This contrasts with a meta coupled version in which more donor acceptor conjugation lowers the triplet energy by 0.2 eV and greatly reduces the rate of reverse intersystem crossing.

According to another aspect of the invention as described herein there is provided a TADF material comprising:
  a TADF molecule as described herein; and
  a solid state host material in which the TADF molecule is disposed.

The solid state host can be selected to have one, more, or all of the following features:
  a highest occupied molecular orbital (HOMO) greater than −5.36 eV and a lowest unoccupied molecular orbital (LUMO) lower than −3.00 eV;
  a triplet level higher than 2.75 eV;
  ambipolarity thereby supporting hole and electron transport;
  a polarity selected to give low energy splitting between $^1CT$ and $^3CT$ of the TADF molecule such that an energy gap between $^1CT$ and $^3CT$ of the TADF molecule does not exceed 0.2 eV, e.g. by providing a solid state host with a polar P=O group.

For example, the solid state host bis-4-(N-carbazolyl) phenyl phenylphosphine oxide (BCPO) exhibits all of the aforementioned features. Such hosts do not quench the TADF emitter molecules as described herein resulting in high solid state photoluminescence quantum yield.

According to yet another aspect of the present invention there is provided an electronic device comprising:
  an anode;
  a cathode; and
  a TADF material as described herein disposed between the anode and cathode.

The electronic device is optionally an organic light emitting diode (OLED) with a maximum external quantum efficiency (EQE) which exceeds 20%, more preferably exceeding 30%. It has been found that TADF materials as described herein provide highly efficient OLED devices. Furthermore, the OLEDs have a low roll-off such that they exhibit an EQE which exceeds 4%, more preferably exceeding 8%, at a brightness of 10,000 $cd/m^2$. Further still, the OLEDs exhibit a TADF brightness level of greater than 15000 $cd/m^2$ and more preferably greater than 18000 $cd/m^2$. Such high values of brightness are commonly observed in phosphorescent devices but not in TADF devices.

TADF molecules as described herein are based upon a reversal of the central acceptor—peripheral donor motif typically found in current TADF emitters as described in the background section. TADF molecules as described herein retain an approximate three-fold symmetry similar to the Tri-PXZ-TRZ molecule of Tanaka, but are configured to have a central electron donor and peripheral acceptor units. Such a configuration can provide a number of advantages as set out below.

Providing a rigid central donor core surrounded by acceptor units can aid in increasing stability and lifetime through the shielding effect of the multiple acceptors attached to the central core.

The acceptor moieties bonded to the central core via nitrogen atoms twist so as to each form a torsion angle between a main plane of the central unit and the main plane of each acceptor moiety. The torsion angle can lie in a range 40° to <90°, optionally 40° to 80°, and optionally 50° to 70°. This torsion reduces overlap between donor and acceptor orbitals and leads to a small energy gap between the singlet and triplet excited states ($\Delta E_{ST}$) desirable for reverse intersystem crossing and improved TADF. Furthermore, embodiments can still have a torsion angle significantly less than 90° which helps to give a good compromise between $^1CT$ ground state coupling for high photoluminescence quantum yield but does not open up a significant $^1CT$-$^3CT$ energy gap. That is, the primary fluorescent mode is not unduly compromised while increasing the TADF mode efficiency. In addition, the vibrational modes of the molecular system should be such as to provide vibrational modes which drive efficient reverse intersystem cross and improved TADF while reducing or eliminating vibrational modes which contribute to non-radiative decay.

An example of a TADF molecule as described herein comprises a triazatruxene (TAT) central donor moiety and three dibenzothiophene-S,S-dioxide ($DBTO_2$) acceptor moieties bonded to the central triazatruxene via the three N-atoms of the triazatruxene. The rigid central donor core limits vibrational modes leading to non-radiative transitions and a decrease in fluorescence efficiency whereas the multiple peripheral acceptors provide vibrational modes which promote rISC for efficient TADF. In this regard, the multi acceptor single central donor motif imparts a large number of resonant energy states which greatly increases the oscillator strength of the $^1$CT transition and gives a short prompt $^1$CT lifetime with a photoluminescence quantum yield (PLQY) ~1. Moreover, multiple singlet-triplet resonances occur within a narrow energy band which gives rise to a very fast rISC rate >1×10$^7$ s$^{-1}$. The conformational complexity of the molecular configuration may also give rise to different rISC rates as observed in the emission decays, however in devices these optimal photophysical properties translate into an external quantum efficiency (EQE) which exceeds 30% and efficiency roll off which is small even out to a brightness of 10,000 cd m$^{-2}$ and beyond. In addition, and despite initial concerns, it has been found that such molecular systems dissolve well in various different solvents allowing efficient purification and synthesis with high yields. Higher purity can further be achieved by heating at, for example, 370° C. for 72 hours at <5.00 e−6 mbar, to sublime away minor low molecular weight impurities in vacuum sublimation equipment. Thin films for devices can also be readily formed by co-evaporation with suitable hosts.

As previously indicated, the TADF molecules according to the present invention are distinct from those of Tanaka by having a central electron donor moiety and peripheral electronic acceptor moieties. DE102016122122 and CN106432251 disclose a large number of potential molecules which are purported to exhibit thermally activated delayed fluorescence, at least some of which do have a central electron donor moiety (e.g. triazatruxene) and peripheral electron acceptor moieties. However, all example TADF molecules in DE102016122122 have a photoluminescence quantum yield (PLQY) of around 50% or less. Similarly, the efficiency of the molecules disclosed in CN106432251 is also very low giving an EQE of only 3.36%. This contrast with the present invention which provides TADF molecules with a much higher PLQY, e.g. approximately 100%. It is also notable that all examples in DE102016122122 have emission decay times in the range 3 to 65 μs. This is typical of the usual delayed fluorescence lifetimes of TADF emitters in the microsecond timeframe. In contrast, the present invention provides TADF molecules with lower emission decay times in the 100 ns timeframe indicative of a faster rISC and a more efficient TADF.

Embodiments of the present invention are distinguished by providing a combination of a central electron donor moiety bonded to three peripheral acceptor moieties via N-atoms, wherein the molecular structure is such that it fulfils one or more of the following characteristics:
  a high PLQY in a solid state host of >60%, >70%, >80%, >90%, or >95% reflecting a high excited state coupling to the ground state;
  at least one delayed fluorescence decay time of less than 1 microsecond, optionally less than 0.5 or less than 0.1 microseconds;
  a high rate of rISC, e.g at least 1×10$^6$ s$^{-1}$, 5×10$^6$ s$^{-1}$, or 1×10$^7$ s$^{-1}$ (a typical upper bound may be of the order of 5×10$^8$ s$^{-1}$);
  a maximum EQE in an OLED device which exceeds 20%, more preferably exceeding 30%;
  a low roll-off such that EQE in an OLED device exceeds 4%, more preferably exceeding 8%, at a brightness of 10,000 cd/m$^2$;
  a high brightness such that in an OLED device brightness levels of greater than 15000 cd/m$^2$, more preferably greater than 18000 cd/m$^2$, are achieved.

Features of the molecular structure which aid in contributing to the aforementioned characteristics include one or more of the following:
  a torsion angle between the acceptor moieties and the central donor in a range 40° to <90°, optionally at least 40°, 50° or 60° and/or no more than 85°, 80°, or 70°, to provide a compromise which enables both a high excited state coupling to the ground state and a low $\Delta E_{ST}$ to be achieved;
  a high excited state coupling to the ground state;
  a low $\Delta E_{ST}$;
  a plurality of singlet-triplet resonances within a small energy band (e.g. 0.2 eV of each other) giving rise to very fast rISC, advantageously with at least one pair of states within 0.05 eV;
  provision of substantially planar fused multi-ring acceptor moieties, such as DBTO$_2$, which twist into the desirable configuration as previously described and provide the correct balance between high excited state coupling to the ground state and a low $\Delta E_{ST}$.

This new TADF molecular design opens up a new design space for truly high performance, high stability TADF OLEDs.

BRIEF DESCRIPTION OF THE DRAWINGS

Embodiments of the present invention are described by way of example only with reference to the accompanying drawings in which.

DETAILED DESCRIPTION

Herein we describe the design, synthesis, characterisation and photophysical properties of a new class of TADF molecules based on a rigid central donor, for example triazatruxene (TAT), having three acceptors attached to its periphery, for example dibenzothiophene-S,S-dioxide (DBTO$_2$), which aims to overcome many of the issues faced when designing an efficient TADF emitter.

Figure 2:
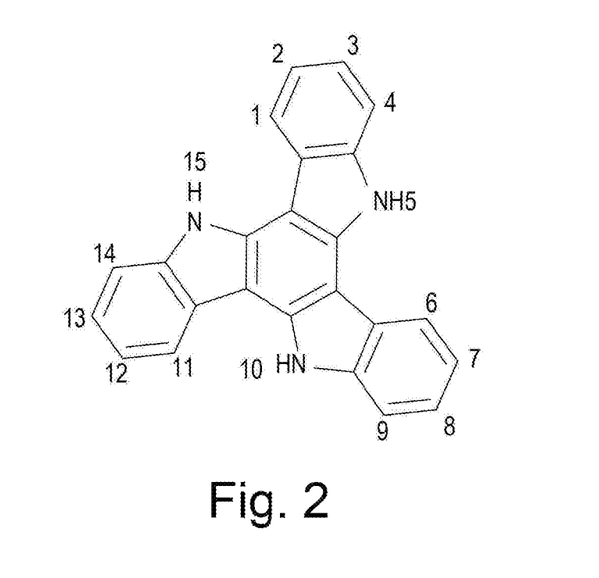
FIG. 2 shows the structure of triazatruxene with position-numbering.

The design of TAT-3DBTO$_2$ is based upon the reversal of the donor and acceptor motif typically found in current TADF emitters. An example of such a prior art configuration is triphenoxazine-2,4,6-triphenyl-1,3,5-triazine (Tri-PXZ-TRZ) which was prepared by Tanaka and co-workers and has a central triazine acceptor unit and three phenoxazine donor units. This work shows the benefits of symmetry as the PXZ-TRZ and bis-PXZ-TRZ analogues showed lower device efficiency compared to the C$_3$ symmetric Tri-PXZ-TRZ. In TAT-3DBTO$_2$, the C$_3$-fold symmetry is maintained as in Tri-PXZ-TRZ, but the donor is a central triazatruxene core onto which three dibenzothiophene-S,S-dioxide units are attached via the nitrogen atom of the core. Dibenzothiophene-S,S-dioxide was chosen as the acceptor to match the energy of the $^3$LE triplet level of the donor to the $^1$CT energy level. Our estimations were based on 2,8-Bis(N(3,6-ditert-butylcarbazolyl)), in which the triplet level of carbazole (D) on dibenzothiophene-S,S-dioxide (A) has a triplet level too high giving a large singlettriplet gap. Triazatruxene is more electron rich than carbazole due to the central 1,3,5-trinitrogen substituted central benzene core, and is also more conjugated. Triazatruxene has been used in non-linear optics, two-photon absorption, organic light emitting diodes (OLEDs), organic photovoltaics (OPVs), organic field-effect transistors (OFETs), organic lasers, as liquid crystalline materials and also in sensors. Triazatruxene has also been well established as a structural feature which can contribute towards efficient hole transport, and with correct functionalisation can have a high photoluminescence quantum yield (PLQY). These excellent properties made it appealing as a potential new donor for an OLED material that emits via a thermally activated delayed fluorescence mechanism. The extended conjugation in triazatruxene compared to carbazole results in a lower triplet energy and therefore a smaller $\Delta E_{ST}$ and faster rISC rate with dibenzothiophene-S,S-dioxide acceptors. Triazatruxene, see FIG. 2, has previously been functionalised in the 2, 7, and 12 positions in many different ways, however little structural diversity in N-substitution has yet been explored to date. The vast majority of N-functionalisation is alkyl-derived to improve solubility. Other N-functionalisation has usually been limited to phenyl or benzyl.

Figure 3:
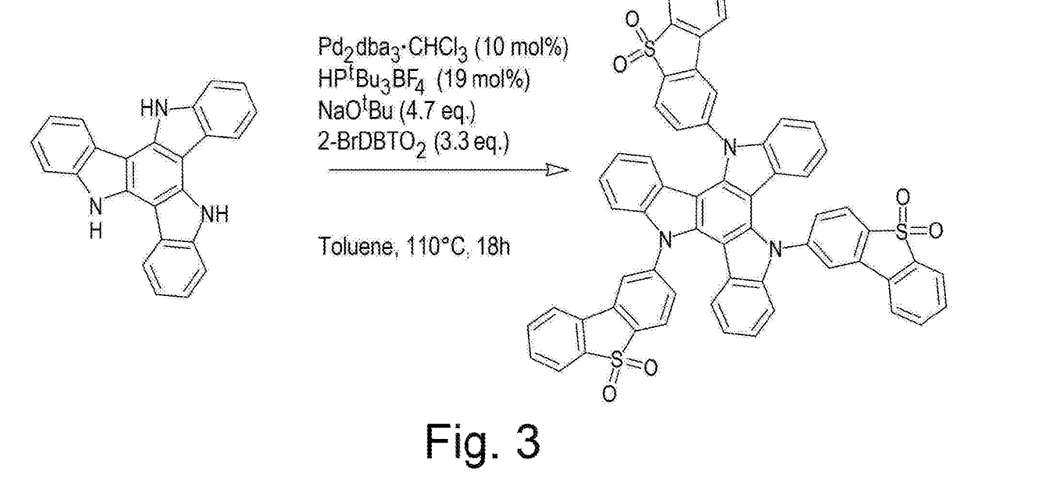
FIG. 3 shows the synthesis of TAT-3DBTO$_2$ via Buchwald-Hartwig coupling conditions.

In the present work, TAT-3DBTO$_2$ was functionalised on the N-position as bonding in this position has typically been shown to give a desirable orthogonal donor and acceptor by twist around the N-C bridge between donor (D) and acceptor (A). The synthesis and structure of TAT-3DBTO$_2$ is shown in FIG. 3.

There were initial concerns about the solubility of TAT-3DBTO$_2$. However this molecule was found to dissolve well in various different solvents allowing for efficient purification and synthesis of the molecule with high yields. The synthesis was surprisingly efficient bearing in mind three Buchwald reactions were performed on one molecule within one reaction overnight.

TAT-3DBTO$_2$ started to show interesting properties from obtaining the first $^1$H NMR spectrum. The $^1$+1 NMR spectrum at room temperature shows a mixture of broad and sharp peaks, suggesting that some of the molecule is rotating slowly on the NMR timescale giving rise to multiple environments for the same protons. This has been shown to be the case by using variable temperature nuclear magnetic resonance spectroscopy (VT NMR) of TAT-3DBTO$_2$ in hexadeuterodimethyl sulfoxide (DMSO-d$_6$), see FIG. 4, and further 2D NMR experiments.

Figure 4:
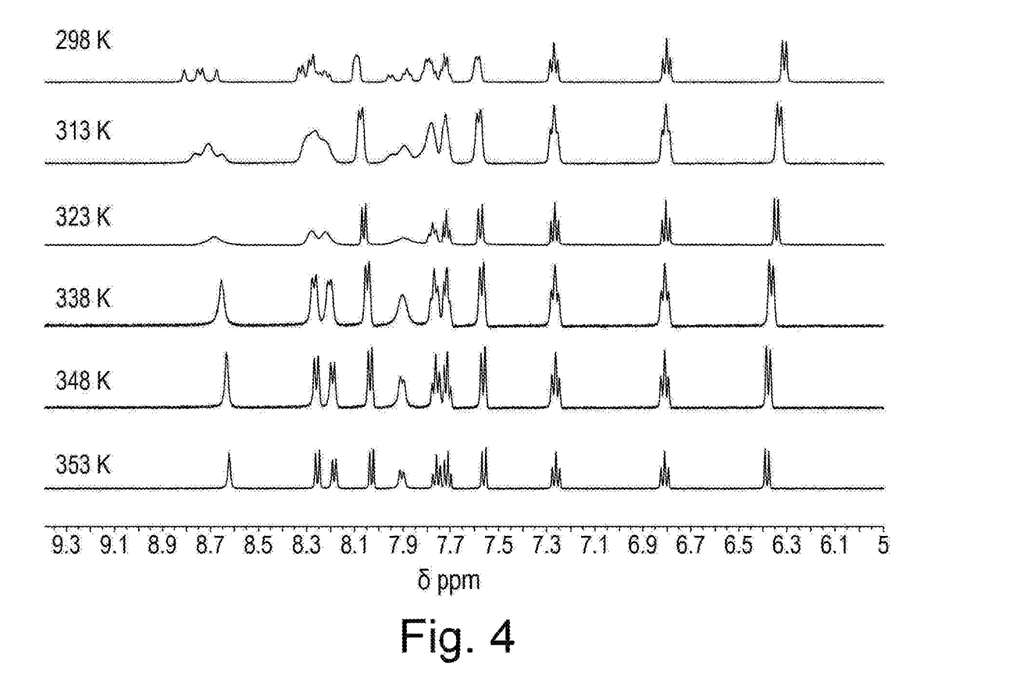
FIG. 4 shows variable temperature nuclear magnetic resonance spectra (VT $^1$H NMR) of TAT-3DBTO$_2$ in hexadeuterodimethyl sulfoxide (DMSO-d$_6$)
Figure 5:
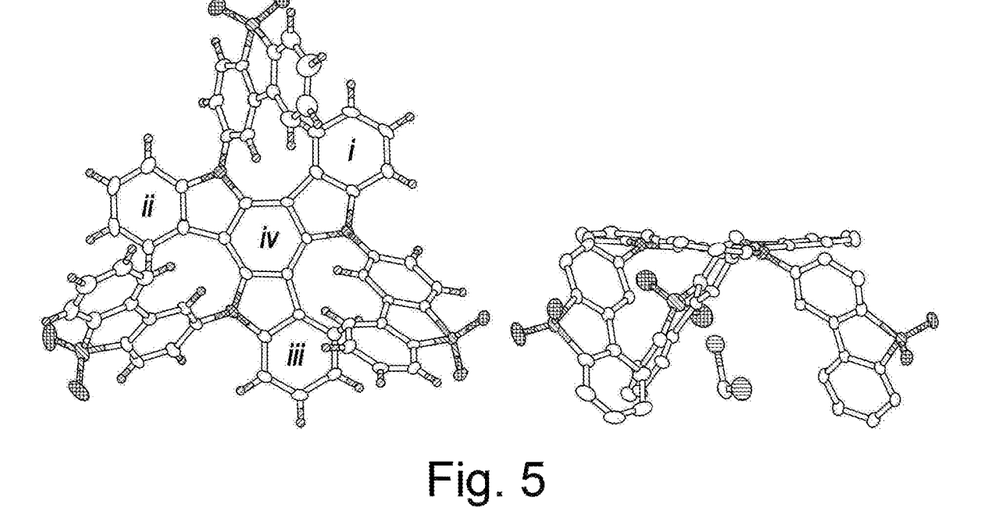
FIG. 5 shows two views of the X-ray crystal structure of TAT-3DBTO$_2$.

The NMR data in combination with pure shift 1H NMR studies shows that there are different conformers of TAT-3DBTO$_2$ in solution and $^1$H ROESY (rotating-frame Overhauser spectroscopy) NMR experiments confirm that these conformers all convert between each other. The NMR data in FIG. 4 shows that there is an energy barrier to rotation around the DA bridging bond and that increasing the temperature to 353K overcomes this barrier. It is suggested these conformers relate to the orientation of the three acceptor units with respect to each other and the triazatruxene core (above and below the core). Crystallisation of TAT-3DBTO$_2$ was challenging and several different crystallisation solvents and techniques had to be used to obtain crystals suitable for X-ray crystallography. The difficulty in growing crystals is desirable for a good OLED emitting material so that amorphous layers with the host can be achieved in devices. FIG. 5 shows two views of the X-ray crystal structure of TAT-3DBTO$_2$ with displacement ellipsoids drawn at a 50% probability level.

TAT-3DBTO$_2$ has no crystallographic symmetry but an approximate local threefold axis. The central fused donor unit is slightly puckered, the outer arene rings i, ii, and iii tilted to one side of the central ring (iv) plane by 6.7, 4.0 and 7.0°, respectively. The three exocyclic NC bonds are tilted to the opposite side of plane iv by 27.0, 26.1 and 23.4°, the three (planar) dibenzothiophene-S,S-dioxide are located on the same side and inclined in a propeller-like fashion, forming dihedral angles of 57.6, 61.9 and 59.8° with plane iv. The resulting intramolecular cavity is occupied by a CHCl$_2$ molecule, while another (disordered) CH$_2$Cl$_2$ molecule fills an inter-host void. Central moieties of inversion-related molecules are stacked face-to-face, at mean separation of ca. 3.6 Å.

The fact that the donor (D) and acceptors (A) have a torsion angle significantly less that 90° is important as it helps to give a good compromise between $^1$CT ground state coupling for high photoluminescence quantum yield (PLQY) while not opening up a significant $^1$CT-$^3$CT gap.

Figure 6:
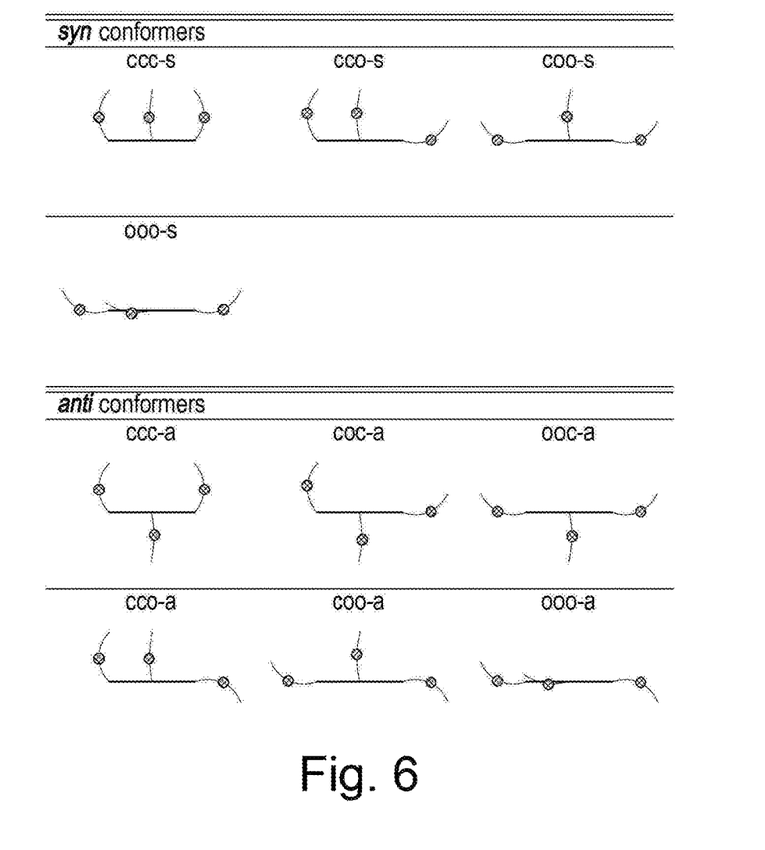
FIG. 6 shows conformers of TAT-3DBTO$_2$ which were found to be within 0.03 eV of each other, reflecting results from NMR.

Structures were optimized with the Q-Chem™ quantum chemistry package using the density functional theory (DFT) method with the Pople's 6-31 G(d) basis set and the Perdew-Burke-Ernzerhof's PBEO functional. Electronic structure calculations were performed using the time dependent TD-DFT method with the 6-31 G(d) basis set and the PBEO functional corrected via the Tamm-Dancoff approximation (TDA). All calculations were performed in gas phase. Twelve possible conformers of the molecule were found within 0.03 eV of each other, reflecting the results from NMR. FIG. 6 shows conformers of TAT-3DBTO$_2$.

Electronic Structure

Absorption

Orbitals H−4, H−3, H−2, H−1 and HOMO are orbitals on the donor part. Orbitals LU MO, L+1, L+2, L+3, L+4 and L+5 are linear combination of orbitals localized on the acceptor moieties. Orbitals L+6, L+7 and L+8 are a combination of orbitals on the donor and orbitals on the acceptors. The absorption spectrum shows four peaks. States S1 to S6 located around 3 eV are mainly composed of excitation from H−1 and H to the first three unoccupied orbitals L, L+1 and L+2. Excited states S7 to S12 around 3.50 eV are excitations from H−1 and H to the three next unoccupied orbitals L+3, L+4 and L+5. A small shoulder at 3.8 eV is comprised of electronic states S13 to S17. Those states mainly involve transitions from H−2 to L, L+1 and L+2 and transitions from H−1 and H to L+6, L+7, L+8. Finally, a third peak around 4.2 eV involves states S18 to S20 that are composed of excitations from H−2 to L+3, L+4, L+5 and H−1 to L+6, L+7, L+8 with a smaller contribution of the H−4 to L excitation. At the ground state equilibrium geometry, the molecular dipole moment is found to be 6 debyes (D).

Emission/Relaxation

To simulate the emission spectra the lowest singlet and triplet states where optimized in the singlet excited state geometry. It is found that for all conformers, one of the acceptors rotates to a more orthogonal geometry with respect to the acceptor in the miminised S$_1$ geometry giving rise to a decreased singlet triplet splitting. Here the lowest singlet and triplet states are very pure charge transfer states. The pairs of states S1-T1 and S2-T2 involve HOMO to LUMO and HOMO-1 to LUMO transitions respectively between the donor and one acceptor unit. States of each pair are nearly degenerate to each other (within 0.1 eV). The Stokes shift in S1 at this geometry is ES-S1=−0.47 eV. The two other pairs involving excitation to each of the other acceptor moieties, S3-T3 and S4-T5 respectively, are higher in energy (ET3=2.66 eV, ES3=2.74 eV, ET4=2.73 eV and ES4=2.77 eV). The two states of each of these pairs are not degenerate as the acceptor involved in the transition is not perpendicular to the donor moiety. Donor and acceptor orbitals have therefore a non-zero overlap resulting in a non-zero interaction between the electron on the donor and the one on the acceptor.

Because the three acceptors seem equivalent, one can expect three minima in S1 corresponding to a transition from the orbital on the donor to acceptor orbital on each acceptor. We thus find that within 0.2 eV of T$_1$ there are 12 excited states, all of which are likely to be vibrationally coupled. If you consider all angular momentum components (all M states) of the triplets, then we may have 30 potentially coupled states involved in rISC. This gives significant enhancement to the rISC rate.

According to the calculations, the wavelength of emission is 578 nm (yellow). Because S1 and T1 are of the same nature, i.e. a HOMO to LUMO transition at the minimum, their minimum energy geometry are very similar. Because of the multiple resonance effect through all the available S$_1$-S$_0$ transitions from the 3 different D-A pairs, we find that the extinction coefficient of TAT-3DBTO$_2$ is 100 times greater than the analogous single D-A material. This major enhancement may also be in part attributed to the D-A torsion angles being somewhat less than 90° yielding significantly more coupling to the ground state. This has pronounced effects on the photophysics of this material.

From these quantum chemistry calculations it is evident that multiple resonance effects between near degenerate transitions and a high density of triplet states that can vibronically couple significantly enhance the photophysical properties of TAT-3DBTO$_2$ which are required for efficient TADF.

Photophysical Properties

In Solution

Figure 7:
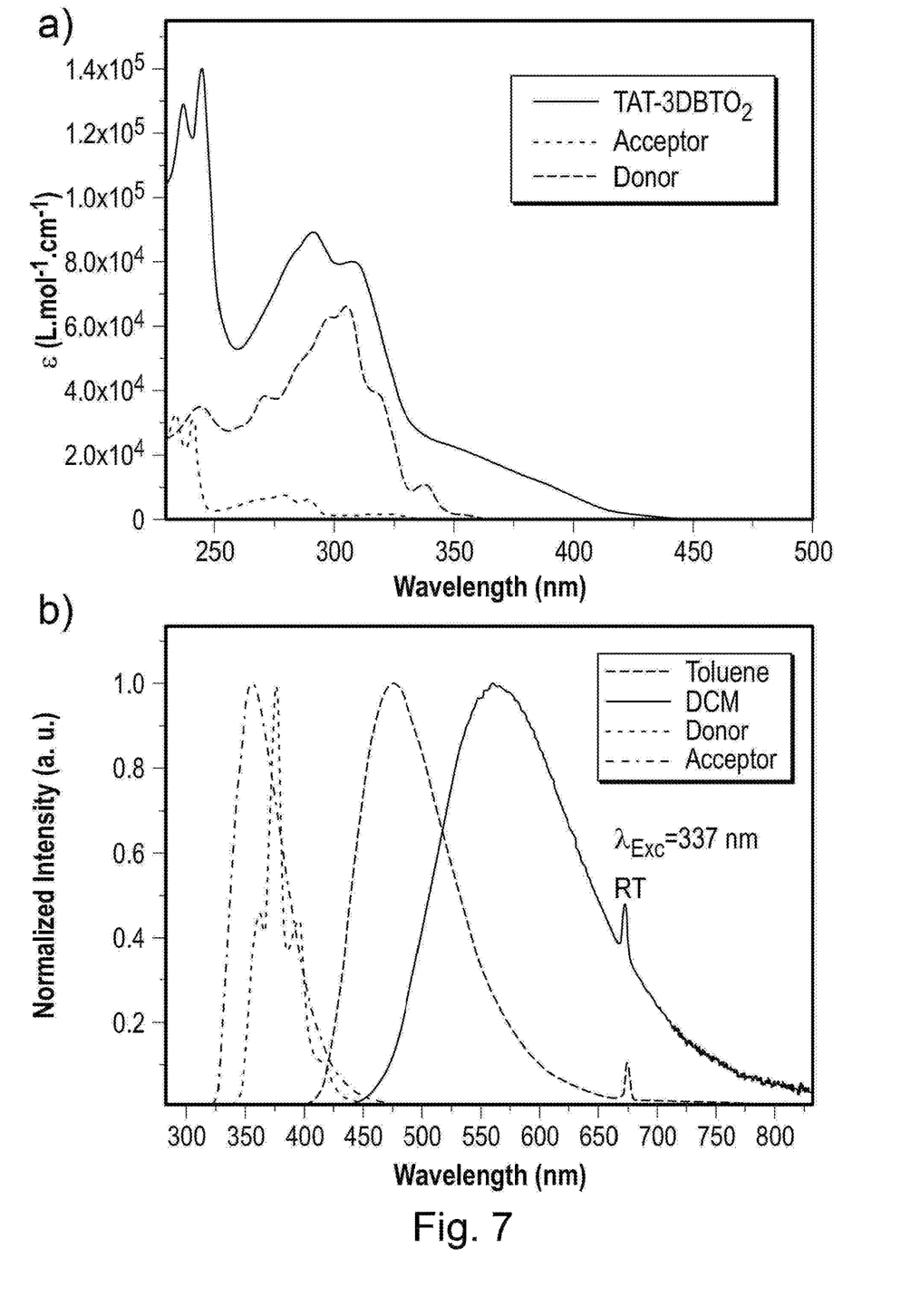
FIG. 7a shows extinction coefficient spectra of TAT-3DBTO$_2$ and the individual D and A units, all in dichloromethane (CH$_2$Cl$_2$) solvent.
FIG. 7b shows photoluminescence (PL) spectra of TAT-3DBTO$_2$ in different solvents together with the D and A units in toluene solution.

FIG. 7a shows the extinction coefficient spectra of TAT-3DBTO$_2$ and that of the individual D and A units, all in dichloromethane (CH$_2$Cl$_2$) solvent. By comparison to the individual D and A units, the extinction coefficient at all the wavelengths is greatly enhanced in TAT-3DBTO$_2$. This increase in oscillator strength reflects very well the prediction from the quantum chemical calculations described above. Particularly the absorption band at lower energy (350 nm to 425 nm) is very strong in this material. This absorption band is not observed in the A or D units and is associated with a direct absorption from the charge transfer (CT) states. A slight red shift is observed on the right edge of the spectra by increasing the polarity of the solvent, which is associated with a strongly mixed n→π*/ππ* character transition, also confirmed by its relatively strong transition. Excitation into this band directly creates $^1$CT excited states.

FIG. 7b shows the photoluminescence (PL) spectra of TAT-3DBTO$_2$ in different solvents together with the D and A units in toluene solution. The spectra show clear and strong charge transfer (CT) emission having a Gaussian band shape and strong red shift compared to the individual D and A emission spectra. The PL spectra move to longer wavelength by increasing the solvent polarity, showing a strong positive solvatochromism.

In Solid state

The charge transfer character of TADF molecules as described herein was also studied in solid state. In addition to the design of the TADF molecule, it can be important to carefully select a solid state host material in which to support the TADF emitter so as to avoid quenching of the TADF emitter. The solid state host can be selected to have one, more, or all of the following features:

(i) a highest occupied molecular orbital (HOMO) greater than −5.36 eV and a lowest unoccupied molecular orbital (LUMO) lower than −3.00 eV;

(ii) a triplet level higher than 2.75 eV;

(iii) ambipolarity thereby supporting hole and electron transport;

(iv) a polarity selected to give low energy splitting between $^1$CT and $^3$CT of the TADF molecule such that an energy gap between $^1$CT and $^3$CT of the TADF molecule does not exceed 0.2 eV, e.g. by providing a solid state host with a polar P=O group.

For example, the solid state host bis-4-(N-carbazolyl) phenyl phenylphosphine oxide (BCPO) exhibits all of the aforementioned features. Other hosts such as mCP (1,3-Bis (N-carbazolyl)benzene), TSPO1 (diphenylphosphine oxide-4-(triphenylsilyl)pheny) and DPEPO (Bis[2-(diphenylphosphino)phenyl]ether oxide) show suitable HOMO-LUMO levels (i) and suitable triplet levels (ii). The most suitable host material will depend to some extent on the specific TADF emitter molecule being utilized.

BCPO (bis-4-(N-carbazolyl)phenyl)phenylphosphine oxide) was chosen as the most suitable host for TAT-3DBTO$_2$ due to the low energy splitting between $^1$CT and $^3$LE and also because of the high photoluminescence quantum yield (PLQY) ~100% measured for TAT-3DBTO$_2$ in BCPO. This excellent PLQY in solid state again reflects the high excited state coupling to the ground state.

Figure 8:
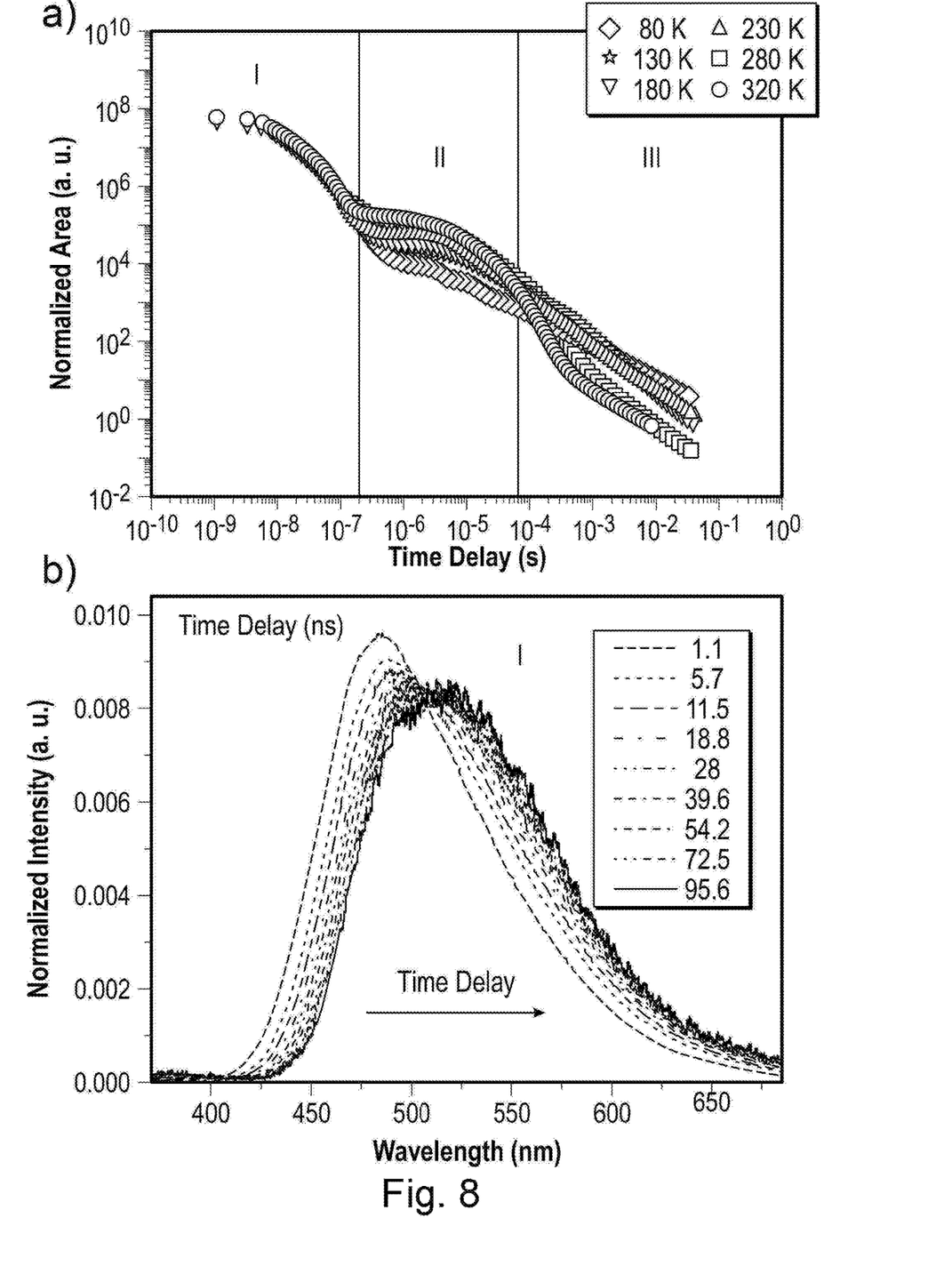
FIG. 8a shows time resolved emission decay curves of TAT-3DBTO$_2$ in a (bis-4-(N-carbazolyl)phenyl)phenylphosphine oxide (BCPO) host indicating three different regimes for the decay curves: region I—fast decay, associated with prompt charge transfer (CT) emission (Prompt Fluorescence—PF); region II—initial delayed fluorescence (DF); and region III—long-lived DF.
FIGS. 8b to 8d show area-normalized emission spectra in region I, II, and III at 320 K.

FIG. 8a shows the time resolved emission decay curves of TAT-3DBTO$_2$ in BCPO host. The decay curves show three different regimes: region (I) fast decay, associated with prompt charge transfer emission (PF); region (II) early times of delayed fluorescence (DF); and region (III) long-lived DF. The PF decay curves do not show temperature dependence, and the decay curve at 320 K was fitted using a bi-exponential: $\tau_1$=10 ns=4.4) and T2=35 ns (12=1.2), consequently, $\tau_{average}$=22 ns. Region II shows strong TADF emission, the delayed fluorescence emission increasing in intensity with increasing temperature because of the increase in available thermal activation energy. The decay times related to region II were $\tau_1$=103.9 ns (42777), $\tau_2$ =3.2 is (I$_2$ 112006) and $\tau_3$=15.1 is (I$_3$=61040) consequently, $\tau_{average}$=11.7 µs. Usually, DF lifetimes of TADF emitters are in the µs time frame whereas TAT-3 DBTO$_2$ shows one DF lifetime in the 100 ns timeframe, which leads to a very fast k$_{rISC}$. We note that the measured PLQY for TAT-3DBTO$_2$ in BCPO is ca. 1, thus this is not a quenched component. Region III has an inverse temperture dependence with the intensity of the emission increasing as the system temperature drops. The behavior of the temperature dependence in this region was observed before in high efficient TADF molecules, and it is associated with longer lived DF component at low temperatures.

The reverse intersystem crossing rates of a TAT-3DBTO$_2$:BCPO film (320 K) were calculated using two different approaches, (see equations 1a and 1b below). Approach (a), relates the k$_{rISC}$ with the triplet formation yield ($\Phi_{ISC}$), which was measured at 37%. Approach (b), relates k$_{rISC}$ with the integrated area of the PF and DF emission, $\int I_{PF}(t)dt$ and $\int I_{DF}(t)dt$, respectively found from the decay curves. The integrated area of DF emission was evaluated in the region where the TADF mechanism is stronger (region II).

$$a)\ k_{rISC} = \frac{1}{\tau_{DF}} \frac{1}{(1-\Phi_{ISC})};$$

$$b)\ k_{rISC} = \frac{\int I_{DF}(t)dt}{\int I_{PF}(t)dt} \cdot \frac{1}{\tau_{DF}}$$

Equation 1 a,b

Three different values of k$_{rISC}$ were calculated (see Table 1 below), each value associated with a distinct lifetime of DF in a TAT-3DBTO$_2$:BCPO film. The fastest lifetime of the DF emission ($\tau_3$) gives very high k$_{rISC}$ rates, even faster than those observed in phosphorescent emitters containing rare metals. This fast value of k$_{rISC}$ will directly translate into devices with excellent efficiency roll-off as will be shown in the device results. Both methods show good agreement to evaluate k$_{rISC}$.

TABLE 1

| | k$_{rISC}$ (eq. 1a) | k$_{rISC}$ (eq 1b) |
|---|---|---|
| $\tau_1$ = 103.9 ns | 1.5 × 10$^7$ s$^{-1}$ | 1.3 × 10$^7$ s$^{-1}$ |
| $\tau_2$ = 3.2 µs | 4.9 × 10$^5$ s$^{-1}$ | 4.3 × 10$^5$ s$^{-1}$ |
| $\tau_3$ = 15.1 µs | 1.0 × 10$^5$ s$^{-1}$ | 9.2 × 10$^4$ s$^{-1}$ |

FIG. 8b shows the area-normalized emission spectra in region I at 320 K. The PF emission shows a continuous dynamic red shift. This red shift is associated with the energetic relaxation of the CT state, primarily due to rotation about the D-A bridging N—C bond as it twists towards a more orthogonal geometry as identified in the quantum chemistry calculations, which stabilizes around 70 ns. Thus, only the transition $^1$CT→S$_0$ is observed. Region II, see FIG. 8c at 320 K, shows stabilized $^1$CT emission and the onset of all spectra collected in this region are at 2.78±0.02 eV. The intensity dependence of the DF emission in this region was analyzed as a function of the laser excitation dose, and a linear gradient of 1 was found. This result confirms the thermally assisted mechanism as opposed to triplet-triplet annihilation (TTA).

FIG. 8d shows the area normalized spectra of region III, at 320 K. At earlier times of this region (edge of the exponential decay), the same emission as that in region II is observed and at later times a very weak emission is detected. Likely, this region includes the DF emission from many different conforms, as the TAT-3DBTO$_2$ molecules has ten distinct conformers close in energy within 0.03 eV and may have some weak phosphorescence (PH) emission.

Figure 9:
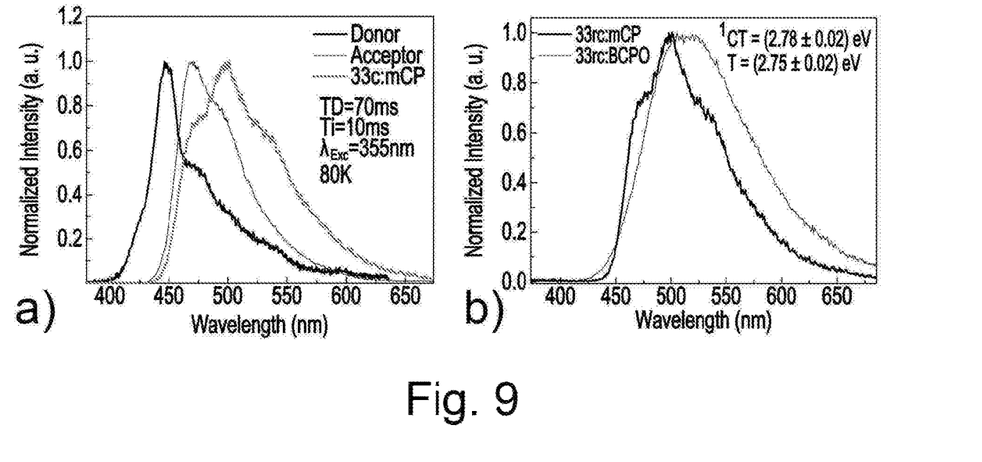
FIG. 9a shows the phosphorescence (PH) spectrum of a TAT-3DBTO$_2$:mCP (1,3-Bis(N-carbazolyl)benzene) film and also the phosphorescence spectrum of the A and D units.
FIG. 9b shows the phosphorescence spectrum together with the photoluminescence spectrum of TAT-3 DBTO$_2$: BCPO.

The same spectral analyses were made at 80 K to identify the PH emission. However, in BCPO host, the harvesting of excitons from triplet to the singlet states is efficient even at low temperatures. DF emission from $^1$CT was detected and any clear PH spectrum was not identified. Thus, we investigate the PH spectrum in mCP because in this host the $\Delta E_{ST}$ is larger, (0.22±0.03) eV and at low temperature (80K) the PH spectrum was clearly identified. FIG. 9a shows the PH spectrum of a TAT-3DBTO$_2$:mCP film and also the PH spectrum of the A and D units. The PH spectrum of TAT-3DBTO$_2$ shows mostly $^3$LE character from the acceptor units, however a peak around 550 nm is strongly enhanced. Comparing the intensities of the vibronic components of the phosphorescence may indicate a perturbed geometry for the LE triplet state in TAT-3DBTO$_2$ compared to the isolated acceptor unit. Considering that the localised triplet states, $^3$LE, are unaffected by the polarity of the host environment, the triplet levels of TAT-3DBTO$_2$ in BCPO host will have the same onset as in mCP host.

FIG. 9b shows the PH spectrum together with the PL spectrum of TAT-3DBTO$_2$:BCPO for better comparison. The $^1$CT states has onset energy at (2.78±0.02) eV and the triplet states at (2.75±0.02) eV, leading to $\Delta E_{ST}$=0.03 eV. Therefore, it is clear that for TAT-3DBTO$_2$ in BCPO host, the $^1$CT state energy lies very close to the triplet states yielding a very small $\Delta E_{ST}$, and consequently, fast rISC and high efficient TADF mechanism.

OLED Performance

To evaluate the potential of TAT-3DBTO$_2$:BCPO in OLEDs, two distinct devices were produced, one designed for optimization of maximum EQE values (OLED 1) and another aiming for low roll-off (OLED 2). The architectures differ just by the ratio (x:y) between host:guest, i. e., for optimization of maximum EQE, a lower amount of TAT-3DBTO$_2$ was co-evaporated with BCPO host (1:9), and for optimization of low roll-off the ratio of TAT-3DBTO$_2$ was higher (1.7:8.3). The architecture of the optimized devices was: ITO/NPB (40 nm)/TCTA (10 nm)/TAT-3DBTO$_2$:BCPO (30 nm)/TPBi (40 nm)/LiF (1 nm)/Al (100 nm). NPB (N,N'-bis(naphthalene-1-yl)-N,N'-bis(phenyl)-benzidine) and TCTA (tris(4-carbazoyl-9-ylphenyl)amine)) were used as commercial hole transport layers, TPBi (1,3,5-tris(N-phenylbenzimidazol-2-yl)benzene) as an electron transport layer, LiF (lithium fluoride) as an electron injection layer and Al (Aluminium) was used as a cathode.

Figure 10:
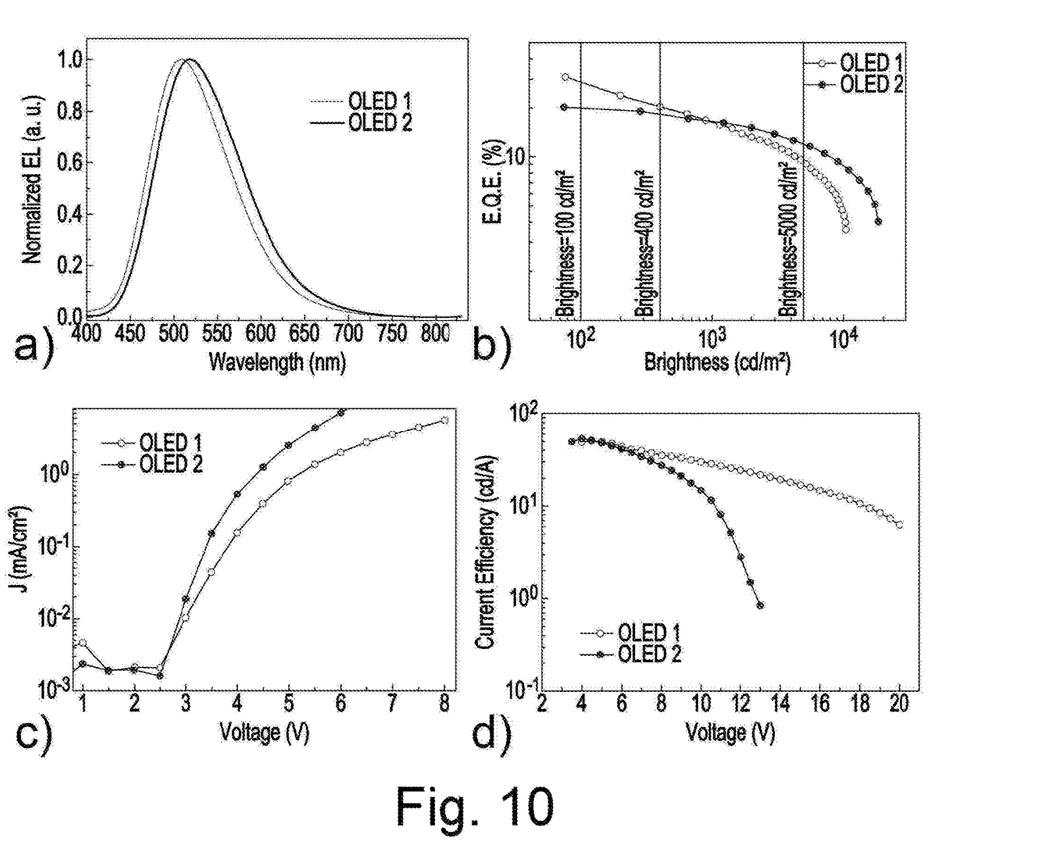
FIG. 10a shows green electroluminescence (EL) spectra of two OLED devices collected at 10 V, one designed for optimization of maximum EQE values (OLED 1) and another aiming for low roll-off (OLED 2)
FIG. 10b shows external quantum efficiency (EQE) versus brightness curves of the two OLED devices.
FIG. 10c shows current density versus voltage of the two OLED devices.
FIG. 10d shows current efficiency (qc) versus voltage curves for the two OLED devices.

FIG. 10a shows the green electroluminescence (EL) spectra of both devices collected at 10 V. The commission internationale de l'eclairage (CIE) chromaticity coordinates (CIEx,CIEy) for these EL spectra are (0.26,0.46) and (0.29, 0.50) for OLED 1 and OLED 2, respectively. OLED 2 is slight red shifted, and it may be associated to the increase in the overall polarity of the emissive layer as a result of increased TAT-3DBTO$_2$ concentration.

FIG. 10b shows the E.Q.E. versus brightness curves. OLED 1 shows maximum EQE value of 30.9% (76 cd/m$^2$). The EQE of an OLED is described by equation 2 below as the product between the charge balance factor, $\gamma$, the fraction of spin-allowed excitons, $\eta_{ST}$, the photoluminescence quantum yield, $\Phi_{PL}$, and the outcoupling efficiency, $\eta_{out}$, which is usually estimated to be 20-30%.

$$EQE = \gamma \cdot \eta_{ST} \cdot \Phi_{PL} \cdot \eta_{out} \qquad \text{Equation 2}$$

Given that $\Phi_{PL}$ was found to be 1 and the high EQE values, we can conclude that: the device has a charge balance close to unity ($\gamma$=1); all the excitons are harvested from the triplet to the singlet states, i.e, 100% TADF efficiency ($\eta_{ST}$=1); and assuming $\eta_{out}$~0.3, which may imply that TAT-3DBTO$_2$ molecules can induce some degree of orientation in the device. At 1.000 cd/m$^2$ OLED 1 shows an EQE above 15%, exhibiting good resistance to roll-off with maximum brightness values up to 10.000 cd/m$^2$ (EQE=4.4%). By increasing the amount of TAT-3DBTO$_2$ molecules in the emissive layer (OLED 2), the maximum EQE values drops to 20.2% (74 cd/m$^2$), but a more efficient roll-off is observed, i.e., the EQE decreases less while increasing the brightness levels. At 10.000 cd/m$^2$, OLED 2 shows an EQE of 8.8%, with brightness levels reaching 18410 cd/m$^2$ (EQE=3.9%). Such high values of brightness are commonly observed in phosphorescent devices, but not in TADF devices.

FIG. 10c shows current density versus voltage for the two OLED devices. Both OLEDs show very low turn-on voltage, around 2.5 V. However, in OLED 1 this value is slightly lower, which may be associated with the fact that TAT-3DBTO$_2$ molecules are not as ambipolar as BCPO, so by decreasing its concentration, a better JV curve (lower turn-on voltage) is observed. The same explanation can be used for the current efficiency ($\eta_c$) versus voltage curves (FIG. 10d) where, up to 8 V, both devices show similar current efficiency ($\eta_{c1,MAX}$=50.8 cd/A, $\eta_{c2,MAX}$=52.9 cd/A) and after that, OLED 1 exhibits much better resistance to high current efficiency levels.

TAT-3DBTO$_2$ introduces a new design for TADF emitters. The rigid donor central core increases stability and lifetime through the shielding effect of the multiple acceptors attached to the triazatruxene core nitrogen sites. The multi acceptor single donor motif imparts a large number of resonant energy states which greatly increases the oscillator strength of the $^1$CT transition and gives a short prompt $^1$CT lifetime with a PLQY ~1. Moreover, we find 12 singlet triplet resonances within 0.2 eV of each other which we believe is what gives rise to a very fast rISC rate>1×10$^7$ s$^{-1}$. The conformational complexity of the molecule may also give rise to different rISC rates as observed in the emission decays, however in devices these optimal photophysical properties translate into an EQE which exceeds 30% and efficiency roll off which is small even out to 10,000 cdm$^{-2}$. Thus, this new TADF molecular design opens up a new design space for truly high performance high stability TADF OLEDs.

Additional Experimental Detail

Three types of samples were studied in this work: (i) TAT-3DBTO$_2$ solutions (10$^{-3}$ to 10$^{-5}$ M) in methylcyclohexane (MCH), toluene and dichloromethane (DCM) solvents; (ii) drop-casting blend film of TAT-3DBTO$_2$:mCP 1:9 molar ratio; and (iii) evaporated doped films of TAT-3DBTO$_2$:BCPO 1:9 v:v. All the solutions were diluted in different solvents and stirred for several hours. The films were dispersed onto quartz substrates.

Steady state absorption and emission spectra were acquired using a UV-3600 Shimadzu spectrophotometer and a Jobin Yvon Horiba Fluoromax 3, respectively. Time resolved spectra were obtained by exciting the sample with a Nd:YAG laser (EKSPLA), 10 Hz, 355 nm or by using a Nitrogen laser, 10 Hz, 337 nm. Sample emission was directed onto a spectrograph and gated iCCD camera (Stanford Computer Optics).

OLED devices were fabricated using pre-cleaned indium-tin-oxide (ITO) coated glass substrates purchased from Ossila with a sheet resistance of 20 Ω/cm$^2$ and ITO thickness of 100 nm. The OLED devices had a pixel size of 4 mm by 2 mm or of 4 mm by 4 mm. The small molecule and cathode layers were thermally evaporated using the Kurt J. Lesker-Spectros II deposition chamber at 10$^{-6}$ mbar. All commercial organic compounds were previously purified by vacuum sublimation.

EXAMPLES

The characteristics of TADF molecules as described herein can be tuned by providing one or more functional groups bonded to one or more carbon atoms of the conjugated multi-ring system of the central core donor unit. These additional functional units can be provided to tune the emission characteristics of the molecule and/or to change the solubility and/or processing characteristics of the molecule.

For example, functionalizing the electron donor core moiety of the TADF emitter molecule with $^t$Bu or small alkyl groups para to each core nitrogen atom will slightly red shift the $^1$CT level and allow the use of hosts which do not have a polar P=K group which is otherwise important for host tuning using a TAT-3DBTO$_2$ TADF emitter.

Figure 11:
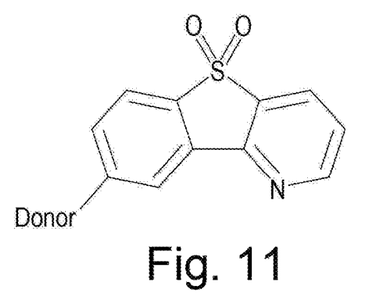
FIGS. 11 to 13 show alternative examples of electron acceptor moieties.

An electron acceptor moiety as illustrated in FIG. 11 may be utilized in place of DBTO$_2$. This modification may also be used to slightly red shift the $^1$CT level without significantly affecting the molecular weight and allow the use of hosts which do not have a polar P=0 group which is otherwise important for host tuning using a TAT-3DBTO$_2$ TADF emitter. The number and position of the nitrogen atoms may also be varied in the structure of FIG. 11.

Figure 12:
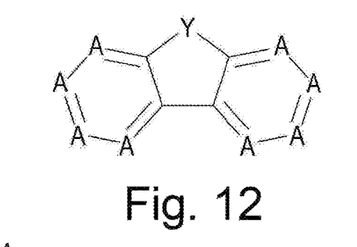
Figure 13:
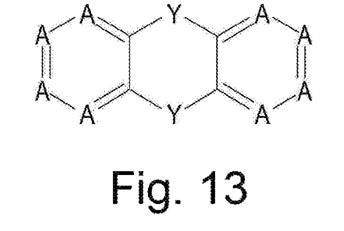

Other options for electron acceptor moieties may include dibenzothiophene-S,S-dioxide, cyanofluorene derivatives, pyrimidines, triazines, and pyridazines so long as the resultant TADF molecular structure achieves the geometry and electronic structure requirements as set out herein. Two possibilities are shown in FIGS. 12 and 13. In the illustrated structures Y may be one of C=O, SO$_2$, SeO$_2$, Ph-P=O, Alkyl, FluoroAlkyl, C(alkyl)$_2$, B(aryl), Si(alkyl)$_2$, or Si(aryl)$_2$. A may be one of CH, D, C(alkyl), C(fluoroalkyl), N, P, C(CN), or CF. Attachment may be via any of the A positions. Again, the structures must be tested to confirm that they result in a TADF molecular structure achieves the geometry and electronic structure requirements as set out herein.

Figure 14:
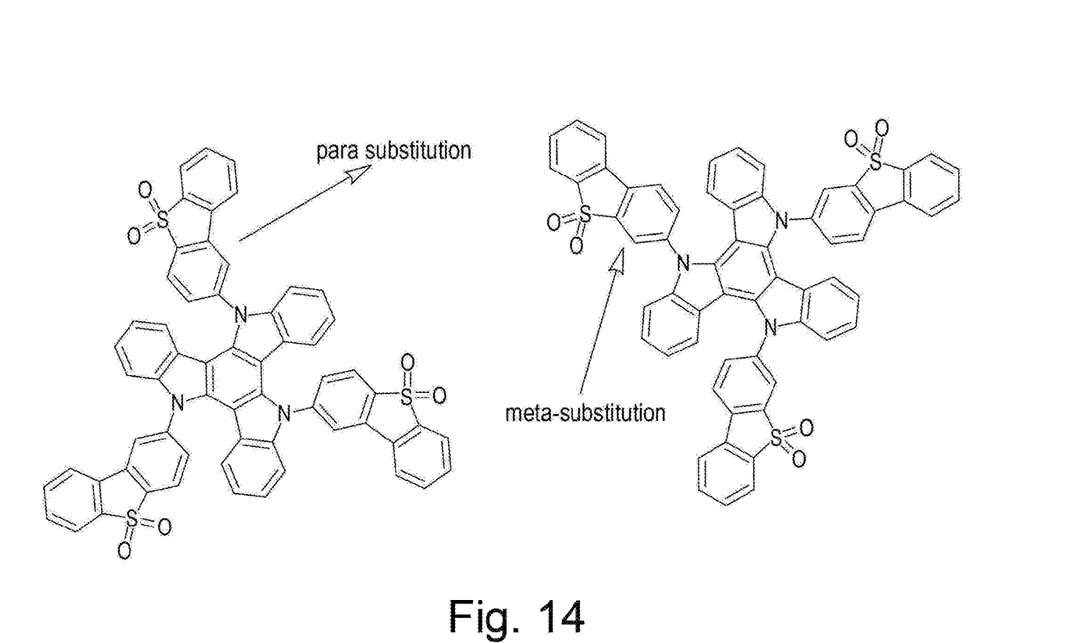
FIG. 14 shows para and meta substituted versions of TAT-3DBTO$_2$.

FIG. 14 shows para and meta substituted versions of TAT-3DBTO$_2$. It has also been found that the substitutional position (on the electron acceptor moieties) of the bond between the central electron donor moiety and the electron acceptor moieties can affect how the electron acceptor moieties are twisted relative to the central electron donor moiety to define the torsion angle in the range 40° to <90° and achieve the required photoluminescence quantum yield and rate of reverse intersystem crossing. In particular, it has been found that for certain configurations it is preferred that the electron acceptor moieties are para substituted rather than meta substituted. For example, in the aforementioned molecular system including a central triazatruxene moiety surrounded by dibenzothiophene-S,S-dioxide (DBTO$_2$) electron acceptor moieties, each (or at least one) DBTO$_2$ moiety is para substituted such that the bond to the nitrogen of the triazatruxene is in a para position relative to the sulphur atom of the DBTO$_2$ moiety. This para coupled version provides a torsion angle in the range 40° to <90° and achieves the required photoluminescence quantum yield and rate of reverse intersystem crossing. This contrasts with a meta coupled version in which more donor acceptor conjugation lowers the triplet energy by 0.2 eV and greatly reduces the rate of reverse intersystem crossing.

While this inventioZn has been described in relation to certain embodiments it will be appreciated that various alternative embodiments can be provided without departing from the scope of the invention which is defined by the appending claims.

REFERENCES

1. W. Y. Park, A. Phadke and N. Shah, *Energ Effic*, 2013, 6, 545-569.
2. F. B. Dias, K. N. Bourdakos, V. Jankus, K. C. Moss, K. T. Kamtekar, V. Bhalala, J. Santos, M. R. Bryce and A. P. Monkman, *Adv. Mater.*, 2013, 25, 3707-3714.
3. Q. S. Zhang, J. Li, K. Shizu, S. P. Huang, S. Hirata, H. Miyazaki and C. Adachi, *J. Am. Chem. Soc.*, 2012, 134, 14706-14709.
4. K. Sato, K. Shizu, K. Yoshimura, A. Kawada, H. Miyazaki and C. Adachi, *Phys. Rev. Lett.*, 2013, 110.
5. J. H. Kim, M. Eum, T. H. Kim and J. Y. Lee, *Dyes Pigm.*, 2017, 136, 529-534.
6. D. Zhang, C. Zhao, Y. Zhang, X. Song, P. Wei, M. Cai and L. Duan, *ACS Appl. Mater. Interfaces*, 2017, DOI: 10.1021/acsami.6b15272.
7. I. Lee and J. Y. Lee, *Org Electron*, 2016, 29, 160-164.
8. G. Z. Xie, X. L. Li, D. J. Chen, Z. H. Wang, X. Y. Cai, D. C. Chen, Y. C. Li, K. K. Liu, Y. Cao and S. J. Su, *Adv. Mater.*, 2016, 28, 181.
9. T. A. Lin, T. Chatterjee, W. L. Tsai, W. K. Lee, M. J. Wu, M. Jiao, K. C. Pan, C. L. Yi, C. L. Chung, K. T. Wong and C. C. Wu, *Adv. Mater.*, 2016, DOI: 10.1002/adma.201601675.
10. P. L. Dos Santos, J. S. Ward, M. R. Bryce and A. P. Monkman, *J. Phys. Chem. Lett.*, 2016, 7, 3341-3346.
11. M. K. Etherington, J. Gibson, H. F. Higginbotham, T. J. Penfold and A. P. Monkman, *Nat Commun*, 2016, 7, 13680.
12. J. Gibson, A. P. Monkman and T. J. Penfold, *ChemPhysChem*, 2016, 17, 2956-2961.
13. J. S. Ward, R. S. Nobuyasu, A. S. Batsanov, P. Data, A. P. Monkman, F. B. Dias and M. R. Bryce, *Chem. Commun.*, 2016, 52, 2612-2615.
14. H. Tanaka, K. Shizu, H. Nakanotani and C. Adachi, *Chem. Mater.*, 2013, 25, 3766-3771.
15. X. C. Li, C. Y. Wang, W. Y. Lai and W. Huang, *J. Mater. Chem. C*, 2016, 4, 10574-10587.
16. T. Techajaroonjit, S. Namuangruk, N. Prachumrak, V. Promarak, M. Sukwattanasinitt and P. Rashatasakhon, *Rsc Adv*, 2016, 6, 56392-56398.
17. E. M. Garcia-Frutos, G. Hennrich, E. Gutierrez, A. Monge and B. Gomez-Lor, *J. Org. Chem.*, 2010, 75, 1070-1076.

The invention claimed is:

1. A thermally activated delayed fluorescence (TADF) molecule comprising:
   a central electron donor moiety, wherein the central electron donor moiety is formed of a conjugated multi-ring system comprising three nitrogen atoms; and
   three electron acceptor moieties, each bonded to the central electron donor moiety via one of the three nitrogen atoms,
   wherein at least one of the three electron acceptor moieties is twisted relative to the central electron donor moiety defining a torsion angle in a range from 40° to less than 90° whereby the TADF molecule has a photoluminescence quantum yield of more than 60% and a rate of reverse intersystem crossing from a lowest excited triplet state to a lowest excited singlet state of at least $1 \times 10^6 s^{-1}$.

2. A TADF molecule according to claim 1, wherein the torsion angle is in a range of 50° to 80°.

3. A TADF molecule according to claim 1, wherein at least two of the three electron acceptor moieties are twisted relative to the central electron donor moiety defining torsion angles in said range.

4. A TADF molecule according to claim 1, wherein the TADF molecule has a plurality of singlet-triplet resonances within 0.2 eV.

5. A TADF molecule according to claim 1, wherein the TADF molecule has at least one pair of singlet charge transfer and triplet charge transfer states within 0.05 eV.

6. A TADF molecule according to claim 1, wherein the rate of reverse intersystem crossing from the lowest excited triplet state to the lowest excited singlet state is at least $1 \times 10^7 s^{-1}$.

7. A TADF molecule according to claim 1, wherein the TADF molecule has at least one delayed fluorescence decay time of less than 1 microsecond.

8. A TADF molecule according to claim 1, wherein the TADF molecule has at least one delayed fluorescence decay time of less than 0.5 microseconds.

9. A TADF molecule according to claim 1, wherein the photoluminescence quantum yield is at least 80%.

10. A TADF molecule according to claim 1, wherein the central electron donor moiety comprises a triazatruxene moiety.

11. A TADF molecule according to claim 1, wherein the central electron donor moiety comprises one or more functional groups bonded to one or more carbon atoms of the conjugated multi-ring system in addition to the three electron acceptor moieties bonded to the nitrogen atoms of the conjugated multi-ring system.

12. A TADF molecule according to claim 10, wherein the central electron donor moiety consists of triazatruxene without any further functional groups bonded to carbon atoms of the conjugated multi-ring system.

13. A TADF molecule according to claim 1, wherein each of the electron acceptor moieties are formed of a conjugated multi-ring system.

14. A TADF molecule according to claim 1,
wherein the electron acceptor moieties are each formed of a conjugated multi-ring system selected such that the TADF molecule has a plurality of singlet-triplet resonances within 0.2 eV with at least one pair of singlet charge transfer and triplet charge transfer states within 0.05 eV.

15. A TADF molecule according to claim 1,
wherein the electron acceptor moieties each comprise dibenzothiophene-S,S-dioxide ($DBTO_2$).

16. A TADF material comprising:
a TADF molecule, the TADF molecule including a central electron donor moiety and three electron acceptor moieties, each bonded to the central electron donor moiety via one of the three nitrogen atoms; and
a solid state host material in which the TADF molecule is disposed,
wherein the central electron donor moiety is formed of a conjugated multi-ring system comprising three nitrogen atoms,
wherein at least one of the three electron acceptor moieties is twisted relative to the central electron donor moiety defining a torsion angle in a range from 40° to less than 90° whereby the TADF molecule has a photoluminescence quantum yield of more than 60% and a rate of reverse intersystem crossing from a lowest excited triplet state to a lowest excited singlet state of at least $1\times10^6 s^{-1}$.

17. A TADF material according to claim 16,
wherein the solid state host is selected to have one or more of the following features:
a highest occupied molecular orbital (HOMO) greater than −5.36 eV and a lowest unoccupied molecular orbital (LUMO) lower than −3.00 eV;
a triplet level higher than 2.75 eV;
ambipolarity thereby supporting hole and electron transport;
a polarity selected to give low energy splitting between $^1CT$ and $^3CT$ of the TADF molecule such that an energy gap between $^1CT$ and $^3CT$ of the TADF molecule does not exceed 0.2 eV.

18. A TADF material according to claim 17, wherein the solid state host is selected to have all of the aforementioned features.

19. A TADF material according to claim 18,
wherein the solid state host is bis-4-(N-carbazolyl)phenyl phenylphosphine oxide (BCPO).

20. An electronic device comprising:
an anode;
a cathode; and
a TADF material disposed between the anode and cathode, the TADF material comprising:
a TADF molecule, the TADF molecule including a central electron donor moiety and three electron acceptor moieties, each bonded to the central electron donor moiety via one of the three nitrogen atoms; and
a solid state host material in which the TADF molecule is disposed,
wherein the central electron donor moiety is formed of a conjugated multi-ring system comprising three nitrogen atoms,
wherein at least one of the three electron acceptor moieties is twisted relative to the central electron donor moiety defining a torsion angle in a range from 40° to less than 90° whereby the TADF molecule has a photoluminescence quantum yield of more than 60% and a rate of reverse intersystem crossing from a lowest excited triplet state to a lowest excited singlet state of at least $1\times10^6$ s$^{-1}$.

21. An electronic device according to claim 20, wherein the electronic device is an organic light emitting diode (OLED) with a maximum external quantum efficiency (EQE) which exceeds 20%.

22. An electronic device according to claim 21, wherein OLED has a maximum EQE exceeding 30%.

23. An electronic device according to claim 21, wherein the OLED has a low roll-off such that it exhibits an EQE which exceeds 4% at a brightness of 10,000 cd/m$^2$.

24. An electronic device according to claim 23, wherein the OLED exhibits an EQE that exceeds 8% at a brightness of 10,000 cd/m$^2$.

25. An electronic device according to claim 21, wherein the OLED exhibits a TADF brightness level of greater than 15000 cd/m$^2$.

26. An electronic device according to claim 25, wherein the TADF brightness level is greater than 18000 cd/m2.

* * * * *